United States Patent [19]

Farago

[11] Patent Number: 4,998,308
[45] Date of Patent: Mar. 12, 1991

[54] SECLUSION ROOM BED

[76] Inventor: Frank Farago, 255 Orleans Way, Long Beach, Calif. 90805

[21] Appl. No.: 479,954

[22] Filed: Feb. 14, 1990

[51] Int. Cl.⁵ ............................................. A61G 7/06
[52] U.S. Cl. ........................................ 5/424; 52/704; 5/503; 5/494; 128/869
[58] Field of Search .................... 52/73, 707, 704; 128/846, 869, 870, 876, 875; 16/DIG. 28; 5/494, 503, 460, 461, 445, 466, 467, 481, 424, 427

[56] References Cited

U.S. PATENT DOCUMENTS

| | | | |
|---|---|---|---|
| 794,457 | 7/1905 | Gaiter | 128/876 |
| 914,785 | 3/1909 | Boyce | 128/869 |
| 1,341,564 | 5/1920 | King . | |
| 1,860,874 | 5/1932 | Triplett | 128/870 |
| 2,456,898 | 12/1948 | Strandhagen | 128/870 |
| 2,556,924 | 6/1951 | Karpen | 5/351 |
| 2,569,561 | 10/1951 | Friedman | 250/57 |
| 2,807,033 | 9/1957 | Austen | 5/461 |
| 2,838,100 | 6/1958 | Follows | 5/481 X |
| 2,846,700 | 8/1958 | De Puy | 128/876 X |
| 2,848,993 | 8/1958 | Terrell | 128/876 X |
| 2,912,977 | 11/1959 | Holbrook | 128/870 |
| 2,959,794 | 11/1960 | Soulelfs | 5/461 |
| 3,209,380 | 10/1963 | Watsky | 5/481 |
| 3,289,224 | 12/1966 | Witchel | 5/466 |
| 3,416,762 | 12/1968 | Headrick | 52/23 X |
| 3,437,089 | 4/1969 | Posey | 128/875 |
| 3,512,191 | 5/1970 | Wall et al. | 5/345 |
| 3,535,718 | 10/1970 | Murcott | 5/494 |
| 3,553,748 | 1/1971 | Ross | 5/481 X |
| 3,757,356 | 9/1973 | Freeman | 4/112 |
| 3,878,844 | 4/1975 | Tobias | 128/876 |
| 3,889,302 | 6/1975 | Ketterer et al. | 4/110 |
| 3,897,778 | 8/1975 | Forbes-Robinson et al. | 128/875 |
| 4,096,594 | 7/1978 | St. Jean | 5/90 |
| 4,106,138 | 8/1978 | Murphy | 5/181 |
| 4,110,881 | 9/1978 | Thompson | 5/481 X |
| 4,275,473 | 6/1981 | Poirier | 9/13 |
| 4,389,741 | 6/1983 | Larson | 5/400 |
| 4,521,928 | 6/1985 | Stephenson | 5/400 |
| 4,620,333 | 11/1986 | Ritter | 5/90 |
| 4,725,270 | 2/1988 | Schuldt et al. | 604/356 |
| 4,745,646 | 5/1988 | Strobel | 5/451 |
| 4,796,316 | 1/1989 | Boselli | 5/464 |

FOREIGN PATENT DOCUMENTS

| | | | |
|---|---|---|---|
| 712542 | 9/1966 | Italy | 128/870 |
| 926722 | 5/1963 | United Kingdom | 128/869 |

Primary Examiner—Eric K. Nicholson
Attorney, Agent, or Firm—Fulwider, Patton, Lee & Utecht

[57] ABSTRACT

A heavy, pliable and substantially indestructible bed for use in conjunction with a stripped room having flush mounted floor anchors to facilitate the restraint of a violent or out-of-control patient during a "time-out" period. Restraints attached to floor anchors adjacent the sides of the bed, are attached to the patient. The lack of hard edges, corners or surfaces prevents injury to the patient and staff during a struggle, while the smooth exterior surfaces eases clean up. A safe and sanitary environment is thereby provided for a seclusion room.

9 Claims, 2 Drawing Sheets

SECLUSION ROOM BED

BACKGROUND OF THE INVENTION

1. Field of the Invention

This invention generally relates to beds, and more particularly, pertains to systems for restraining an out-of-control or violent patient in a reclined position.

2. Brief Description of the Prior Art

The behavior of certain patients undergoing treatment in various institutions may at times require their confinement to a seclusion room for short periods of time in order to insure their own safety as well as the safety of others. Also referred to as time-out rooms or restraint rooms, a variety of different approaches have been employed in the past to provide an adequate facility for such a purpose. While padding or other coverings affixed to the walls and floors do provide some protection and while clinically, they appear humane, sufficient protection is, in fact, not provided thereby in order to prevent an acutely out-of-control control patient from inflicting injury on himself. The use of a camisole (straight jacket) in these rooms does afford slightly more protection, but still necessitates one-to-one staff supervision. An additional shortcoming is inherent in the fact that such padding is easily soiled and can be picked apart, therefore requiring constant and costly upkeep.

An alternate approach comprises the use of a "stripped" room (bare walls and floors) which does provide a more sanitary environment, but requires the use of a special restraint bed for acute patients. The restraint beds are typically of rather conventional construction in that a mattress is supported by a rigid frame. The frame is typically of heavy-duty construction in order to take the substantial loads it may be subjected to, has provisions to facilitate the attachment of restraints thereto, and because it is often bolted to the floor, an entire room may thereby be rendered useful for only a singular purpose. The potential for injury is great during violent episodes, such as when struggling with a resisting patient in an attempt to position him on and restrain him to the bed as lacerations, contusions or even fractures can result when any of the exposed ridges, edges, corners, legs or other hard surfaces are contacted with sufficient force. An additional shortcoming relates to the use of conventional mattresses as they are typically hard to keep clean, difficult to clean when soiled, and consequently, may cause the hygiene of such seclusion rooms to be compromised. Conventional mattresses are additionally susceptible to damage and are costly to replace.

SUMMARY OF THE INVENTION

The present invention seeks to overcome the disadvantages and shortcomings of the prior art as set forth above by providing a safe, hygienic and indestructible bed for use within a stripped room. The bed consists of a self-supporting, monolithic, resilient foam filled structure that is set directly on the floor. A seamless, non-porous and tough but pliable vinyl outer skin covers the entire exterior. The sheer weight and bulk of the bed obviates the need to anchor the bed to the floor. The lack of an external rigid frame, legs, hard edges, corners or seams, in conjunction with the resilience of the foam core and vinyl covering, minimizes the possibility of injury when contacting the bed.

The tough and impervious outer vinyl covering cannot be punctured, scratched or otherwise harmed without the use of a sharp rigid implement. The smooth and non-porous surface can easily be cleaned when soiled.

In a preferred embodiment, the bed of the present invention is used in combination with a stripped room having a plurality of flush mounted floor anchors to which restraints are readily attachable. Once positioned on top of the bed, a patient is restrained by passing appropriately configured restraints from the floor anchors, located adjacent one side of the bed, to ankle, wrist and belly straps worn by the patient. Alternatively, the bed is modified to incorporate loops or tunnels near its top edges through which the restraints are passed serving to more positively restrain the patient by limiting longitudinal movement. Another embodiment of the invention calls for the incorporation of reinforcement about the above-described loops to facilitate the attachment of the restraints directly thereto. A rigid frame integrated within the interior of the foam filled core provides the necessary strength to prevent the pull-out of the loops.

Additional features incorporated in the bed of the present invention include a plurality of parallel grooves in its top surface to promote the drainage of fluid from beneath the patient, and the location of a groove about the entire periphery of the bed to enable fitment of a sheet.

Other features and advantages of the present invention will become apparent form the following detailed description, taken in conjunction with the accompanying drawings, which illustrate by way of example, the principles of the invention.

DETAILED DESCRIPTION OF THE PREFERRED EMBODIMENTS

The restraint bed system of the present invention is intended for use within a stripped room and facilitates the temporary restraint and confinement of a patient undergoing an acute episode. The figures illustrate a number of embodiments of the present invention, wherein the variations pertain to the manner in which restraints cooperate with the bed.

Figure 1:
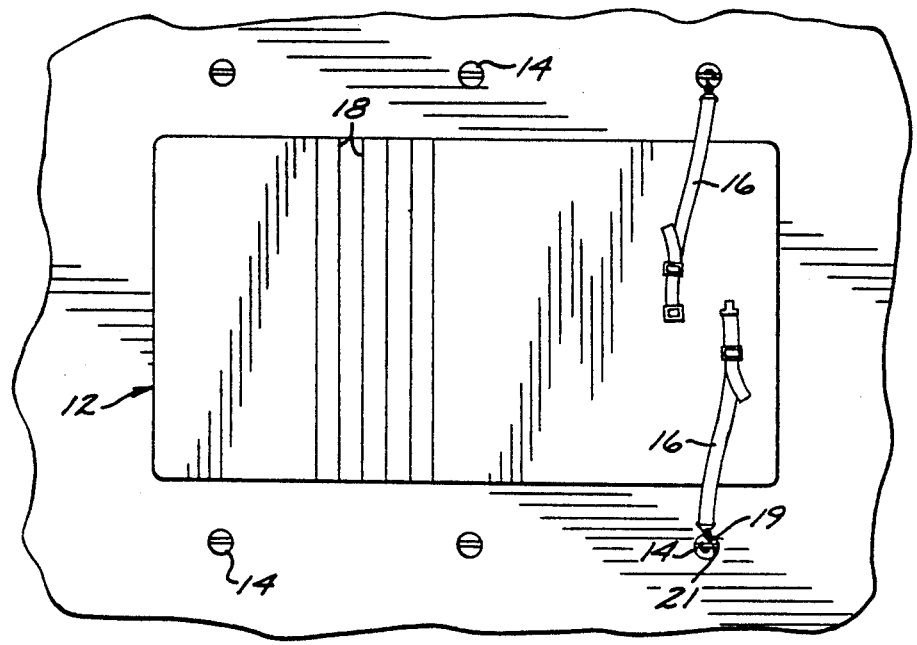
FIG. 1 is a top plan view of a seclusion room bed system according to the present invention.
Figure 2:
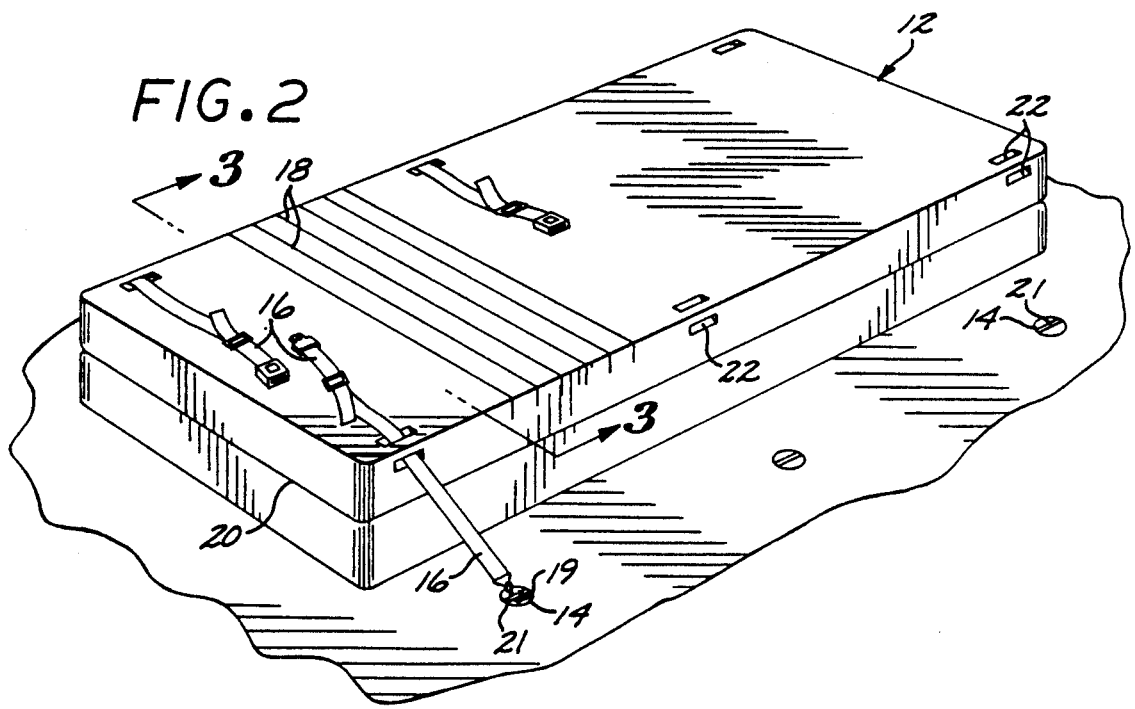
FIG. 2 is a perspective view of an alternate embodiment of the present invention.
Figure 3:
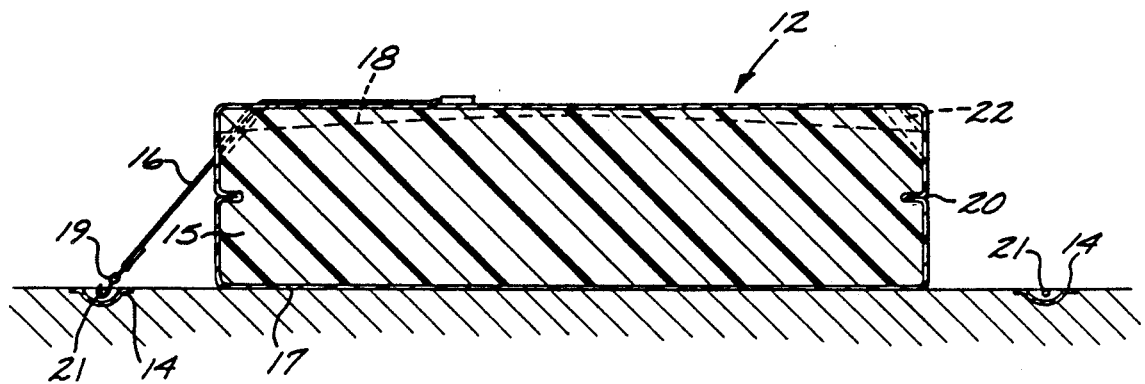
FIG. 3 is a cross-sectional view of FIG. 2 taken along lines 3—3.

FIGS. 1-3 illustrate embodiments of the present invention, wherein the bed 12 is utilized in combination with a plurality of flush mounted floor anchors 14 to which restraints 16 are quickly and easily attachable. A variety of different attachment means are available and can be employed for this particular application. For the purposes of illustration, the figures generally show a hook 19, appropriately affixed to the restraint 16, engaging a horizontally anchored bar 21 positioned within a depression in the floor. The restraints are quickly and easily attached to belly, ankle and wrist straps worn by the patient.

The embodiments illustrated in FIGS. 1-3 all show the same basic structure in that a resilient foam core 15 is encapsulated by a continuous heavy vinyl skin 17 to yield a form nominally 4'×7'×½', in size. The embodiment illustrated in FIG. 2 and 3 incorporates the additional feature not found in FIG. 1 in that a plurality of tunnels 22 extend from the bed's side surfaces to its top surface at positions adjacent each floor anchor. The tunnels 22 are dimensioned to allow the free passage of the restraints 16 therethrough.

Figure 4:
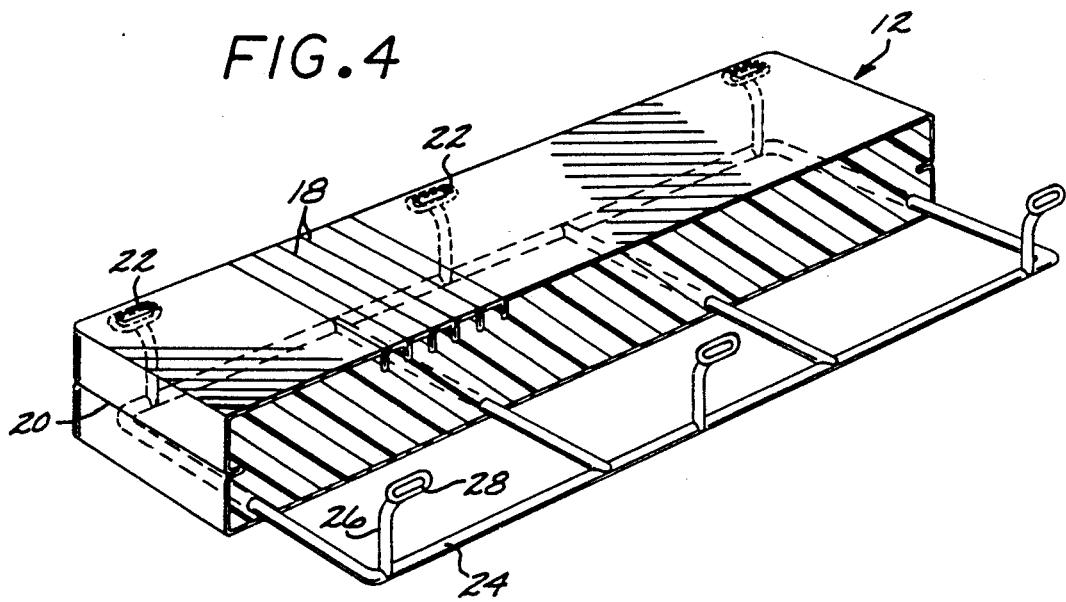
FIG. 4 is a partially cut-back perspective view of another alternate embodiment of the present invention.

The variation of FIG. 4 illustrates the incorporation of a rigid framework 24 within the interior of the foam core 15 to which a plurality of upright extensions 26 are attached. Each extension 26 terminates in an annular structure 28 surrounding or partially surrounding tunnels 22 to provide sturdy reinforcement thereof. This particular embodiment facilitates the attachment of the restraints 16 directly to the bed 12 and enables the bed to be utilized without the above-described floor anchor if preferred.

Each of the embodiments as shown in the figures additionally feature a plurality of parallel depressions or groves 18 in the top surface. As is clearly illustrated in FIG. 3, the depth of each depression or groove increases as the edge of the edge of the bed is approached. An additional groove 20 extends about the entire periphery of the bed at approximately half height.

The exterior of the bed comprises a flexible vinyl covering, approximately 200 mils thick. The vinyl covering is seamless, impervious to liquid, stain resistant and easily cleaned. The highly resilient polyurethane foam core is molded in one piece and bonded to the seamless vinyl covering. A bed constructed of such materials, approximately 7' long 4' wide and 18" high weighs on the order of 250 lbs. The internal frame of the embodiment illustrated in FIG. 4 is preferably of welded metal construction.

In use, the bed is positioned within a stripped room to provide the sanitary and non-stimulatory environment necessary for the handling of an acute patient. The lack of sharp edges or hard surfaces on the bed precludes injury to the patient or staff during a struggle. The use of flush mounted floor anchors similarly minimizes the possibility of injury due to the lack of exposed surfaces or edges. The relatively soft construction of the bed provides a degree of comfort, yet is firm enough to allow the effective use of restraints. Prior to use, the bed may be fitted with a sheet which is tucked into the peripheral groove 20. The embodiments of FIGS. 2-4 require the sheet to be appropriately perforated to allow access to the tunnels 22. Once the patient is properly positioned on the bed, the restraints 16 are attached to the floor anchors 14 and then fastened to the patient. The embodiment of FIG. 4 allows the restraints to be secured directly to the bed as the rigid framework 24, extensions 26 and annular structure 28 cooperate to prevent pull-out. Grooves 18 facilitate the drainage of fluids from beneath the patient. The gradually increasing depth of the grooves as the edges of the bed are approached (FIG. 3) prevents puddling even when a substantial weight is being supported by bed 12. After use the bed is easily cleaned, as upon removal of the sheet, the entire bed can be either hosed down and or scrubbed.

While a particular form of the invention has been illustrated and described, it will also be apparent to those skilled in the art that various modifications can be made without departing from the spirit and scope of the invention. Accordingly, it is not intended that the invention be limited except a by the appended claims.

What is claimed is:

1. A seclusion room facility, for safely controlling a patient undergoing a violent episode, comprising:
   a self-supporting bed wherein all exposed top and side surfaces, edges and corners are pliable and resilient;
   a floor, for supporting said bed, having a plurality of substantially flush-mounted floor anchor means therein and positioned adjacent the side surfaces of said bed;
   restraint means having a first end attachable to said floor anchor means and a second end attachable to a patient reclined on the top surface of said bed for restraining said patient to said bed.

2. The seclusion room facility of claim 1 wherein said bed comprises a substantially monolithic foam core covered by a continuous and seamless, flexible vinyl skin material bonded thereto.

3. The seclusion room facility of claim 2 wherein said bed is formed to define tunnels adjacent said floor anchors extending from the side surfaces to the top surface and dimensioned to accommodate the positioning of said restraint means to extend therethrough.

4. The seclusion room facility of claim 2 wherein said bed's top surface is formed to define grooves, extending from one side surface of the bed to an opposite side surface of the bed, each groove gradually increasing in depth as each side surface is approached.

5. The seclusion room facility of claim 2 wherein said bed's side surfaces are formed to define a continuous horizontal groove extending about the entire periphery of said bed and dimensioned to receive a bed sheet covering the top surface of the bed.

6. The seclusion room facility of claim 2 wherein said bed incorporates a rigid frame in its interior.

7. The seclusion room facility of claims 3 wherein said bed incorporates a rigid frame in its interior.

8. The seclusion room facility of claim 7 wherein said rigid frame includes a structure to reinforce the tunnels to prevent pull out thereof.

9. A seclusion room restraint bed comprising:
   a heavy, self-supporting structure having soft and resilient top and side surfaces, edges and corners and formed to define a plurality of tunnels extending from two opposing side surfaces to the top surface, said bed further comprising an internally disposed rigid frame including structures extending therefrom and configured to reinforce the perimeter of said tunnels to prevent their pull-out.

* * * * *